United States Patent [19]

Childs

[11] 4,169,960
[45] Oct. 2, 1979

[54] REMOVING WATER FROM FLUORINATED ALCOHOLS EMPLOYING A TETRAHYDROCARBYLAMMONIUM HYDROXIDE

[75] Inventor: William V. Childs, Bartlesville, Okla.

[73] Assignee: Phillips Petroleum Company, Bartlesville, Okla.

[21] Appl. No.: 856,549

[22] Filed: Dec. 1, 1977

[51] Int. Cl.² .............................................. C07C 3/34
[52] U.S. Cl. ................................................... 568/842
[58] Field of Search ................................. 568/842, 843

[56] References Cited

U.S. PATENT DOCUMENTS

| 3,151,171 | 9/1964 | Day ....................................... 568/842 |
| 3,317,615 | 5/1967 | Graham ................................. 568/842 |
| 3,449,389 | 6/1969 | Warnell ................................. 568/842 |

OTHER PUBLICATIONS

Fieser, Experiments in Organic Chemistry, 3rd Ed., Heath & Co., Boston, 1957, pp. 48–49.
Weissberger, Tech. of Org. Chem., vol. III, part I, Separation & Purification, Interscience Publishers, New York, 1956, pp. 304–306.

*Primary Examiner*—Howard T. Mars

[57] ABSTRACT

Water is removed from fluorinated alcohols, e.g., fluoroalkanols by intimately contacting the same with a tetrahydrocarbylammonium hydroxide.

13 Claims, No Drawings

REMOVING WATER FROM FLUORINATED ALCOHOLS EMPLOYING A TETRAHYDROCARBYLAMMONIUM HYDROXIDE

This invention relates to the removal of water from a fluorinated alcohol. More specifically, it relates to a process removing water from a fluorinated alcohol by a liquid-liquid contacting operation.

In one of its concepts, the invention provides a process for the removal of water from a fluorinated alcohol in liquid state which comprises contacting the same intimately with a tetrahydrocarbylammonium hydroxide. In a more specific concept of the invention, it provides a process for the removal of water from 1,1-dihydroheptafluorobutanol employing an aqueous solution of tetrabutylammonium hydroxide.

Alcohols, both substituted and unsubstituted have wide chemical application. Fluorinated alcohols are particularly useful in many instances. 1,1-Dihydroperfluoroalkanols, for example, are useful chemical intermediates for incorporating fluoroalkyl groups into a given molecule. For example, 1,1-dihydroheptafluorobutanol, a known compound, is particularly useful for replacing chlorine atoms on a given organic molecule to provide a heptafluorobutoxy substituent. One recent application of this type is the reaction of the sodium salt of 1,1-dihydroheptafluorobutanol with poly(dichlorophosphazene) in a process to produce an elastomer with excellent high and low temperature properties, oil resistance for gaskets, seals, and hoses, all of which are directed toward aircraft applications. The high performance of the aforementioned elastomer depends in part on the purity of the dihydroheptafluorobutanol employed. As the purity decreases, the performance likewise decreases. Hence it is important to obtain the alcohol in the highest purity possible. 1,1-Dihydroheptafluorobutanol is prepared by the reduction of methyl heptafluorobutyrate with sodium borohydride. This reaction mixture is subsequently acidified with an aqueous acid and the alcohol is separated by distillation to a constant boiling (83° C.) mixture of 22 weight percent water and 78 weight percent 1,1-dihydroheptafluorobutanol. Upon cooling the distillate, most of the water can be, and is removed by phase separation. The remaining water/alcohol mixture is again subjected to distillation whereupon the water is slowly removed or reduced in concentration by additional azeotrope separation. As the water content is lowered, the ability to remove additional amounts becomes more difficult and time consuming. It is essential to remove or reduce as much water as possible from the alcohol otherwise it will preferentially react with sodium during the conversion of the dihydroheptafluorobutanol to its sodium salt resulting in unreacted fluoroalkanol in the final elastomer, thus affecting elastomer performance properties.

It is an object of this invention to provide a process for removing water from a fluorinated alcohol. It is another object of the invention to provide a process for the removal of water from a fluorinated alkanol. It is another object of the invention to remove water from 1,1-dihydroheptafluorobutanol. A still further object of the invention is to provide a liquid-liquid contacting operation for removal of water from a fluorinated alcohol.

Other aspects, concepts, objects and the several advantages of the invention are apparent from a study of this disclosure and the appended claims.

According to the present invention water is removed from a fluorinated alcohol by contacting the alcohol in liquid state with a tetrahydrocarbylammonium hydroxide. The contacting is preferably intimately performed. It is now preferred to employ the dewatering agent as an aqueous solution. Upon settling the contacted materials, two phases are formed; the heavier organic phase, generally containing the fluorinated alcohol with only small amounts of water and small amounts of tetrahydrocarbylammonium hydroxide.

It can be seen that separation by the present invention of water from fluorinated alcohol is not only an alternate but potentially a faster method than the one above described involving repeated distillations.

The addition of the tetrahydrocarbylammonium hydroxide to the fluorinated alcohol/water mixture will absorb water from the alcohol/mixture. Depending upon concentrations and conditions some or substantially all of the water can be removed from the alcohol.

The invention is particularly applicable to the removal of water from fluoroalkanols and will now be described with respect to such alcohols.

Fluoroalkanols employed in this invention are represented by the formula

wherein R can be a $C_1$–$C_{10}$ perfluoroalkyl radical and $R_1$ or $R_2$ can be a hydrogen or $C_1$–$C_{10}$ perfluoroalkyl radical. An example of a typical fluoroalkanol useful in this invention is 1,1-dihydroheptafluorobutanol. The fluoroalkanol can contain before the treatment by this invention water ranging from 0.5–25 weight percent but will usually contain water between 1–10 weight percent. Water can be removed from the used hydroxide by simple distillation or by other methods as desired.

Tetrahydrocarbylammonium Hydroxide

The tetrahydrocarbylammonium hydroxides useful in the invention are represented by the formula

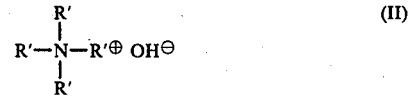

wherein R' is an alkyl or cycloalkyl radical of one to six carbon atoms such as methyl, ethyl, propyl, isopropyl, butyl, isobutyl, pentyl, hexyl and cyclohexyl or mixtures thereof wherein the total number of carbon atoms is at least twelve. Typical nonlimiting examples include, tetrapropylammonium hydroxide, tetraisopropylammonium hydroxide, tetra-n-butylammonium hydroxide, tetra-isobutylammonium hydroxide, tetra-sec-butylammonium hydroxide, tetra-tert-butylammonium hydroxide, tetrapentylammonium hydroxide, tetrahexylammonium hydroxide, tetracyclohexylammonium hydroxide, and the like. In addition, mixtures of the aforementioned ammonium hydroxides can be employed as well as quaternary ammonium hydroxides containing mixed alkyl groups such as dipropyldibutylammonium hydroxide, propyltributylammonium hydroxide, and the like. The concentration of the tetrahydrocarbylammonium hydroxide aqueous solution is considered to be broadly 0.1-2.0 molar and preferably in the range of 0.2-1.2 molar. The ratio of fluoroalkanol/water mixture to tetrahydrocarbylammonium hydroxide aqueous solution will depend in part on the solubility of the tetrahydrocarbylammonium hydroxide in the fluoroalkanol and the water in which it is dissolved and on the amount of water present in the fluoroalkanol/water mixture. One skilled in the art can make a determination of optimum conditions, including ratio by mere routine test.

The equipment and procedures used in the invention can be various. One method can be to add the aqueous tetrahydrocarbylammonium hydroxide solution to the fluoroalkanol/water mixture at a temperature in the approximate range of 20° C. to 80° C., preferably at or near ambient room temperature, rapidly stir, mix, or shake the two mixtures in such a manner so as to cause an intimate contact between all ingredients, allow the mixtures to stand at the operating temperatures employed until a satisfactory liquid two-phase separation occurs and to then separate the two liquid layers, the lighter aqueous phase generally containing the tetrahydrocarbylammonium hydroxide and water with only trace amounts of the fluoroalkanol and the heavier organic phase generally containing the fluoroalkanol with small amounts of water and tetrahydrocarbylammonium hydroxide.

EXAMPLE 1

This example illustrates the current invention. To 1.40 grams of a liquid containing 91.14 weight percent 1,1-dihydroheptafluorobutanol and 8.86 weight percent (0.124 grams) water (determined by chromatography) was added 0.68 grams of a 1.0 molar aqueous solution of tetrabutylammonium hydroxide. The combined mixture was intimately mixed in a small glass separatory funnel for a few minutes and then allowed to stand still for a few more minutes to permit liquid two-phase separation. The bottom heavies layer (1.73 grams) was removed and analyzed by gas-liquid chromatography (GLC) using a 4.27 m (14 ft) Porapak (Trademark) PS column programed between 15C to 250C at a rate of 30C/min. The analysis indicated; 93.9% 1,1-dihydroheptafluorobutanol, 2.6% pentafluoropropanol, and 3.5% (0.06 grams) water. GLC analysis of the top layer (0.35 grams) indicated 99+% water. Thus, by calculations, 48.39 weight percent of the original water present in the fluoroalkanol liquid remained in the organic bottom layer while 51.61 weight percent of the original amount of water in the fluoroalkanol liquid was removed.

EXAMPLE 2

This example illustrates the inoperability of an inorganic strong base to separate water from fluoroalkanol/water mixtures. A mixture (1 ml) of 1,1-dihydroheptafluorobutanol/methyl alcohol was treated with 1 ml of 0.5 molar aqueous sodium hydroxide in the same manner as described in Example 1. GLC analysis of the bottom organic layer indicated a large absorption of water (approximately 14 percent) rather than desorption of water as illustrated in Example 1 where tetrabutylammonium hydroxide was employed.

EXAMPLE 3

This example illustrates the water absorption ability of 1,1-dihydroheptafluorobutanol. Water-free 1,1-dihydroheptafluorobutanol (1 ml) was treated with 1 ml of 1.0 molar aqueous tetrabutylammonium hydroxide in the same manner as described in Example 1. GLC analysis of the bottom organic layer indicates the presence of approximately 23 percent water.

The preceding examples show that an aqueous solution (1.0 molar) of a tetrahydrocarbylammonium hydroxide can extract water from a fluoroalkanol/water mixture.

To the extent that the dewatering agent is concentrated initially, it can remove more water. Even a solid agent can be employed.

Reasonable variation and modification are possible within the scope of the foregoing disclosure and the appended claims to the invention the essence of which is that water is removed from a fluorinated alcohol employing a tetrahydrocarbylammonium hydroxide, e.g., an aqueous solution thereof.

What is claimed is:

1. A process for removing water from a fluorinated alcohol containing water in an amount in the approximate range 0.5-25 wt % which comprises contacting the same intimately with an aqueous solution of a tetrahydrocarbylammonium hydroxide to substantially reduce the water in said fluorinated alcohol, and allowing formation of phases to occur and then separating the phases, wherein the alcohol is one represented by the formula

wherein R is selected from a perfluoroalkyl radical having 1-10 carbon atoms and $R_1$ and $R_2$ are selected from a hydrogen and a perfluoroalkyl radical having 1-10 carbon atoms and wherein the tetrahydrocarbylammonium hydroxide is represented by the formula

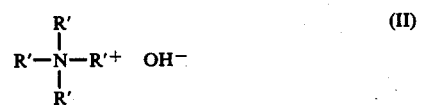

wherein R' is selected from alkyl and cycloalkyl radicals having 1-6 carbon atoms.

2. A process according to claim 1 which comprises contacting it with an aqueous solution of a tetrahydrocarbylammonium hydroxide.

3. A process according to claim 1 wherein the tetrahydrocarbylammonium hydroxide is selected from tetrapropylammonium hydroxide, tetraisopropylammonium hydroxide, tetra-n-butylammonium hydroxide, tetra-isobutylammonium hydroxide, tetra-sec-butylammonium hydroxide, tetra-tert-butyl-ammonium hydroxide, tetrapentylammonium hydroxide, tetrahexylammonium hydroxide, and tetracyclohexylammonium hydroxide.

4. A process according to claim 3 wherein the tetrahydrocarbylammonium hydroxide is tetrabutylammonium hydroxide.

5. A process according to claim 1 wherein the compound from which water is removed is a fluorinated alkanol.

6. A process according to claim 5 wherein the tetrahydrocarbylammonium hydroxide is selected from tetrapropylammonium hydroxide, tetraisopropylammonium hydroxide, tetra-n-butylammonium hydroxide, tetra-isobutylammonium hydroxide, tetra-sec-butylammonium hydroxide, tetra-tert-butylammonium hydroxide, tetrapentylammonium hydroxide, tetrahexylammonium hydroxide, and tetracyclohexylammonium hydroxide.

7. A process according to claim 5 wherein the tetrahydrocarbylammonium hydroxide is tetra-n-butylammonium hydroxide.

8. A process according to claim 1 wherein the fluorinated alcohol is a 1,1-dihydroperfluoroalkanol.

9. A process according to claim 2 wherein the alcohol is a fluorinated alkanol.

10. A process according to claim 2 wherein the alcohol is a 1,1-dihydroperfluoroalkanol.

11. A process according to claim 2 wherein the concentration of the aqueous solution of the tetrahydrocarbylammonium hydroxide is in the range of 0.1–2 molar.

12. A process according to claim 1 wherein the fluorinated alcohol is a 1,1-dihydroperfluoroalkanol and the tetrahydrocarbylammonium hydroxide is selected from tetrapropylammonium hydroxide, tetraisopropylammonium hydroxide, tetra-n-butylammonium hydroxide, tetra-isobutylammonium hydroxide, tetra-sec-butylammonium hydroxide, tetra-tert-butylammonium hydroxide, tetrapentylammonium hydroxide, tetrahexylammonium hydroxide, and tetracyclohexylammonium hydroxide.

13. A process according to claim 12 wherein the tetrahydrocarbylammonium hydroxide is tetra-n-butylammonium hydroxide.

* * * * *